United States Patent [19]

Hosaka et al.

[11] Patent Number: 5,179,620
[45] Date of Patent: Jan. 12, 1993

[54] STRUCTURE OF NEEDLE-TYPE LENS

[75] Inventors: Hidehiro Hosaka; Kohei Ono; Shinji Yamamori; Tadashi Nakayama; Yoji Sato; Hideya Katayama, all of Tokyo, Japan

[73] Assignee: Nihon Kohden Corporation, Tokyo, Japan

[21] Appl. No.: 714,948

[22] Filed: Jun. 13, 1991

[30] Foreign Application Priority Data

Jun. 15, 1990 [JP] Japan .................... 2-62702[U]

[51] Int. Cl.⁵ .................................... G02B 23/26
[52] U.S. Cl. .................................... 385/147; 385/117; 385/119
[58] Field of Search ............... 350/96.10, 96.18, 96.20; 385/33, 76, 117, 119, 146, 147; 359/36, 435

[56] References Cited

U.S. PATENT DOCUMENTS

| | | | |
|---|---|---|---|
| 4,148,550 | 4/1979 | MacAnally | 359/435 |
| 4,281,929 | 8/1981 | Lord et al. | 385/117 |
| 4,732,450 | 3/1988 | Lee | 350/96.18 |
| 4,921,326 | 5/1990 | Wild et al. | 385/117 |
| 4,930,851 | 6/1990 | Yamamoto | 350/96.10 |
| 4,974,924 | 12/1990 | Okada et al. | 350/96.20 |
| 4,988,158 | 1/1991 | Yamamoto | 350/96.18 |

FOREIGN PATENT DOCUMENTS

0416371A2 8/1990 European Pat. Off. .
WO8605964 10/1985 PCT Int'l Appl. .

Primary Examiner—John D. Lee
Assistant Examiner—Phan T. Heartney
Attorney, Agent, or Firm—Sughrue, Mion, Zinn, Macpeak & Seas

[57] ABSTRACT

A needle type lens structure comprises, an inner tube having a relay lens inserted therein, an outer tube mounted around an outer periphery of the inner tube in concentric relation thereto with a predetermined gap, and light transmitting device, for guiding illumination light to the distal end of the needle type lens, provided axially between the inner tube and the outer tube.

3 Claims, 2 Drawing Sheets

STRUCTURE OF NEEDLE-TYPE LENS

BACKGROUND OF THE INVENTION

This invention relates to the structure of a needle-type lens for observing a living body.

A conventional needle-type lens for observing the interior of a living body is constructed as shown in FIGS. 4 to 6. In these Figures, a relay lens 2 of a bar-like shape is inserted in an inner tube 1, and a support member 3 of a generally cylindrical shape is mounted on one end of the inner tube 1. An ocular lens 4 is mounted within the support member 3, and is disposed on the optical axis of the relay lens 2. A solid charge-coupled device (CCD) (not shown) is connected to the end of the support member 3 remote from the end thereof on which the inner tube 1 is mounted. A funnel-shaped condenser guide 5 made of an acrylic resin is mounted on the outer periphery of the inner tube 1 in intimate contact therewith. The proximal end portion of this condenser guide is increasing in diameter, and fits on the outer periphery of the support member 3, and is fixed thereto by a plurality of fixing screws 6.

In the needle-type lens 7 of the above construction, its distal end is inserted into a portion of a living body to be observed, and light emitted from a light source (not shown) is applied via the condenser guide 5 to the portion to be observed, and an image of the observed portion is projected onto the CCD in a magnified manner through the relay lens 2 and the ocular lens 4. The image projected on the CCD is converted into an electrical signal, and is displayed on a display device via a processing circuit.

In the conventional needle-type lens structure of the above construction it is difficult to manufacture the condenser guide 5, because an acrylic resin must be formed into an elongated tubular shape. Furthermore, the surface of this condenser guide can be easily damaged resulting in light leading through the damaged portion. The condenser guide has further drawbacks in that it may be deformed upon the lapse of time and, it can be corroded by chemicals. As a result, there is a risk that the portion to be observed will not be illuminated sufficiently.

As described above, in the conventional needle-type lens structure, it, is difficult to manufacture the condenser guide, which is formed into an elongated tubular shape, using an acrylic resin. Furthermore, the condenser guide can be damaged at its surface, and is corroded by chemicals and/or deformed. As a result, sufficient illumination can not always be provided.

SUMMARY OF THE INVENTION

The present invention has been made in view of the above problems, an objective of the invention to provide a needle-type lens structure which can be easily manufactured, is excellent in durability, and can sufficiently illuminate the portion to be observed.

The above objective has been achieved by a needle-type lens attached to an image pickup probe which contains a charge-coupled device provided at a central portion thereof, and a light guide member provided around said charge-coupled device, and opening to one end face; CHARACTERIZED in that said light guide member is constituted by a plurality of light-transmitting fibers; said needle-type lens is constituted by an inner tube having a relay lens inserted therein, an outer tube fixedly mounted around an outer periphery of said inner tube in concentric relation thereto, and said plurality of light-transmitting fibers provided axially between said inner tube and said outer tube so as to guide illumination light to the distal end of said needle-type lens; the proximal end of said outer tube is increased in diameter and is connected to the end face of said probe; and the light-transmitting fibers on the side of said probe are communicated respectively with the light-transmitting fibers on the needle-type lens at their connection ends.

In the above construction, light from a light source is applied via the optical fibers to a portion to be observed. Thus, this portion may be sufficiently illuminated. Furthermore, since the optical fibers are protected by an outer tube, durability is enhanced.

DETAILED DESCRIPTION OF THE PREFERRED EMBODIMENTS

The invention will now be described with reference to the drawings.

Figure 1:
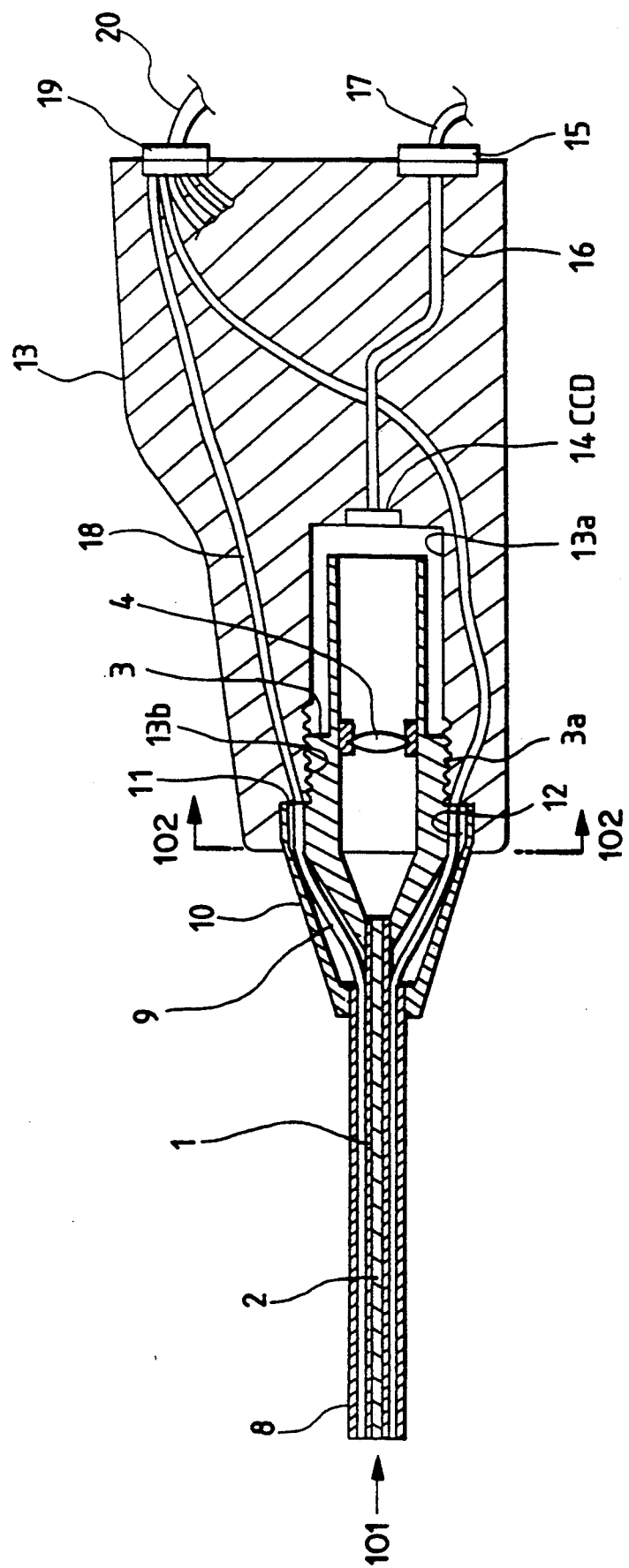
FIG. 1 is a vertical cross-sectional view of the preferred embodiment of a needle-type lens structure of the present invention.
Figure 2:
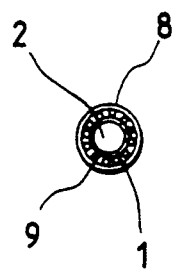
FIGS. 2 and 3 are views as viewed from arrows 101 and 102 of FIG. 1, respectively.
Figure 3:
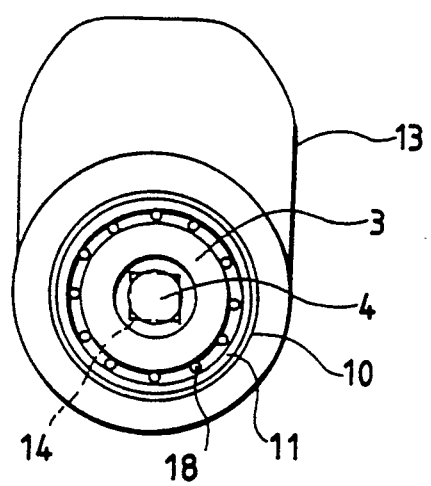
Figure 4:
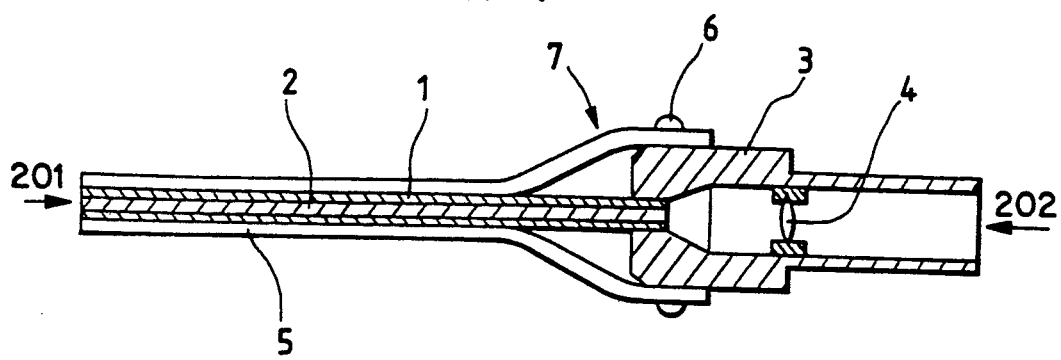
FIG. 4 is a vertical cross-sectional view of a conventional needle-type lens structure.
Figure 5:
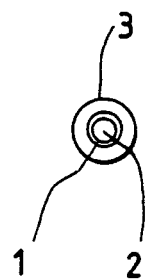
FIGS. 5 and 6 are views as viewed from arrows 201 and 202 of FIG. 4, respectively.
Figure 6:
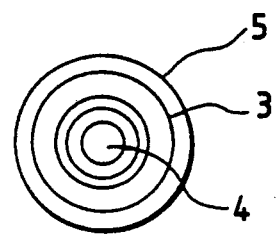

FIGS. 1 to 3 show a preferred embodiment of the invention. Those portions of these Figures identical to or corresponding to those of the prior art of FIGS. 4 to 6 are designated by identical reference numerals, respectively, and explanation thereof will be omitted.

Features of this embodiment include an outer tube 8 mounted around an outer periphery of an inner tube 1 (in which a relay lens (bar-shaped lens) 2 is inserted) in concentric relation thereto, with a predetermined gap provided therebetween, and a plurality of optical fibers 9 inserted axially through the space between the inner tube 1 and the outer tube 8. The proximal end of the outer tube 8 is fixedly secured to a support member 3 through a cover 10 of a generally conical shape. A flange portion 11 is provided at the connection between the support member 3 and the cover 10, and a plurality of (for example, twelve) parallel through holes 12 are formed axially through the flange, portion 11 at equal intervals. The support member 3 has male threads 3a on an outer circumference thereof which act to fixedly source the support member to one end face of the image pick up probe 13 on which is disposed a circular recess 13a having an inner diameter approximating the outer circumference of the threaded support member and in which the internal circumference has female threads 13b to accept the male threads of the support member. Twelve optical fibers 9, 18 are passed respectively through the through holes 12 into the space between the inner tube 1 and the outer tube 8. The distal ends of the optical fibers 9, 18 are open to the, distal ends of the inner and outer tubes 1 and 8. The twelve optical fibers 9, 18 extend from through holes 12 in flange portion 11, to a proximal end of the image pick up probe where they are collected and fed through the body of the image pick up probe via a bushing 19, bundled together in one fiber bundle 20 and connect to a light source (not shown). An ocular lens 4 is mounted within the support member 3, and is disposed on the optical axis of the relay lens 2. A solid charge-coupled device (CCD) 14 is centrally located along an optical axis of the relay lens with an electrical lead 16 running from the CCD to a proximal end of the image pick up probe, exiting the body of the image pick up probe via a bushing 15 and cable 17 to further circuitry (not shown). The inner tube 1, the outer tube 8, the support member 3 and the cover 10 are all made of stainless steel.

In this embodiment, light emitted from the light source passes through the optical fibers 9, 18 and efficiently illuminates a portion of a living body to be observed against which portion the distal ends of the inner and outer tubes 1 and 8 are abutted. Since the inner tube 1 and the outer tube 8 are made of stainless steel, these tubes each having a small diameter and a long axial length can be precisely manufactured. Further, since the optical fibers 9 are covered with the outer tube 8, the optical fibers 9 are prevented from damage, corrosion, deformation, etc.

In the above embodiment, although the various parts are made of stainless steel, this material is not limited to stainless steel. The number of the optical fibers 9, 18 as well, as the number of the through holes 12, is not limited to twelve.

As described above, in the present invention, the needle-type lens is constituted by the inner tube and the outer tube, and the optical fibers are inserted through the space between the two tubes. Therefore, this structure can be manufactured easily and precisely, its durability is enhanced, and the portion to be observed can be sufficiently illuminated.

What is claimed is:

1. An elongate, invasive, needle type lens structure for observing an interior of a living body, comprising:
    an inner tube (1);
    one or more image light transmitting relay lenses (2) disposed within said inner tube;
    a protective outer tube (8) mounted around an outer periphery of said inner tube in concentric relation thereto with a predetermined gap formed therebetween;
    a plurality of illumination light transmitting optical fibers (9) for guiding illumination light to a distal end of said needle type lens, said fibers being disposed axially and circumferentially spaced within said predetermined gap formed between said inner and outer tubes; and
    an image pick up probe (13) comprising:
        a charge-coupled device (14) centrally located along an optical axis of said relay lens;
        light guide members (18) provided around said charge coupled device and extending to one end face of said image pick up probe;
        an ocular lens (4) disposed on said optical axis of said relay lens; and
        a cover (10) connecting a proximal end of said outer tube to said one end face of said image pick up probe.

2. A needle type lens structure as claimed in claim 1, wherein a proximal end of said inner tube is connected to said one end face of said image pick up probe.

3. A needle type lens structure as claimed in claim 2, wherein said light transmitting means is communicated between said image pick up probe and said cover.

* * * * *